(12) United States Patent  
Conger (10) Patent No.: US 8,011,980 B2
(45) Date of Patent: Sep. 6, 2011

(54) SIDE-LOADING COMPACT CRIMP TERMINATION

(75) Inventor: Steven R. Conger, Agua Dulce, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/562,072

(22) Filed: Sep. 17, 2009

(65) Prior Publication Data

US 2011/0065307 A1    Mar. 17, 2011

(51) Int. Cl.
*H01R 4/10* (2006.01)

(52) U.S. Cl. .................................................. 439/877

(58) Field of Classification Search .......... 439/882, 439/881, 877; 174/84 C, 94 R
See application file for complete search history.

(56) References Cited

U.S. PATENT DOCUMENTS

| 3,077,027 | A | * | 2/1963 | Sola et al. ................. 29/866 |
| 3,364,460 | A | * | 1/1968 | Bergan ..................... 439/882 |
| 6,018,683 | A | | 1/2000 | Verness et al. |
| 7,228,624 | B2 | | 6/2007 | Culp |
| 7,383,090 | B2 | | 6/2008 | O'Brien et al. |
| 2005/0085884 | A1 | | 4/2005 | O'Brien et al. |
| 2006/0057904 | A1 | * | 3/2006 | Sakaguchi et al. ........... 439/877 |
| 2007/0149048 | A1 | | 6/2007 | O'Brien et al. |
| 2007/0173115 | A1 | | 7/2007 | O'Brien et al. |

FOREIGN PATENT DOCUMENTS

| EP | 1525899 A2 | 4/2005 |
| EP | 1525899 A3 | 4/2005 |

* cited by examiner

*Primary Examiner* — Phuong K Dinh (57) ABSTRACT

An implantable medical lead comprising a conductor extending along the lead and a crimp connector secured to the conductor comprising a body with an outer surface, an inner surface, proximal and distal ends, and first and second lateral edges, the lateral edges having edge features extending there from, the edge features adapted to opposingly interleave with one another. Methods of assembling a crimp connector with a cable conductor including parallel and cross-wise assembly are also encompassed.

14 Claims, 10 Drawing Sheets

SIDE-LOADING COMPACT CRIMP TERMINATION

FIELD OF THE INVENTION

The present invention relates to medical apparatus and methods of manufacturing such apparatus. More specifically, the present invention relates to implantable cardiac electrotherapy leads and methods of manufacturing such leads. More particularly, the present invention relates to crimp terminations on lead conductors.

BACKGROUND OF THE INVENTION

Current implantable cardiac electrotherapy leads (e.g., cardiac resynchronization therapy ("CRT") leads, bradycardia leads, tachycardia leads) utilize crimp connectors to transition from conductor cables to a wide range of features on or around the lead including electrodes, shock coils and the like. These crimp connectors often take the form of a tube like structure through which the cable conductor or conductors may be fed or threaded. Once properly placed along the length of the conductor or conductors, the crimp connector may be crimped to secure its position.

In some instances, feeding or threading the conductor through the crimp connector is not feasible due to geometrical constraints, process constraints, such as prior connections at one or both ends of a conductor, access constraints, or other constraints known to those in the art. Additionally, the narrow nature of the vasculature and the maintenance of blood flow limit the space available for the lead. As such, space efficient devices are desirable.

There is a need in the art for a space efficient crimp connector that can be placed on a conductor without feeding or threading the conductor there through. There is also a need in the art for a method of employing such a crimp connector.

SUMMARY

In one embodiment, an implantable medical lead may include a conductor extending along the lead and a crimp connector secured to the conductor. The crimp connector may include a body with an outer surface, an inner surface, proximal and distal ends, and first and second lateral edges. The lateral edges may have edge features extending there from where the edge features are adapted to opposingly interleave with one another. In another embodiment, the edge features may include staggered complimentary projections. The crimp connector may be adapted for parallel or cross-wise assembly. In another embodiment, the crimp connector may include an extension attached to and extending from the distal or proximal end of the body. The extension may include a microcoil attachment feature.

In another embodiment, a method of attaching a crimp connector to a cable conductor on an implantable medical lead may include positioning the crimp connector adjacent to the cable conductor, displacing the crimp connector perpendicular to a longitudinal axis of the cable conductor thereby receiving the cable conductor with the crimp connector, and crimping the crimp connector with a crimp tool. In another embodiment, the method may include orienting the crimp connector parallel to the cable conductor. In another embodiment, the method may include orienting the crimp connector perpendicular to the cable conductor. In still another embodiment, the method may include pivoting the crimp connector from a perpendicular position to a parallel position.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
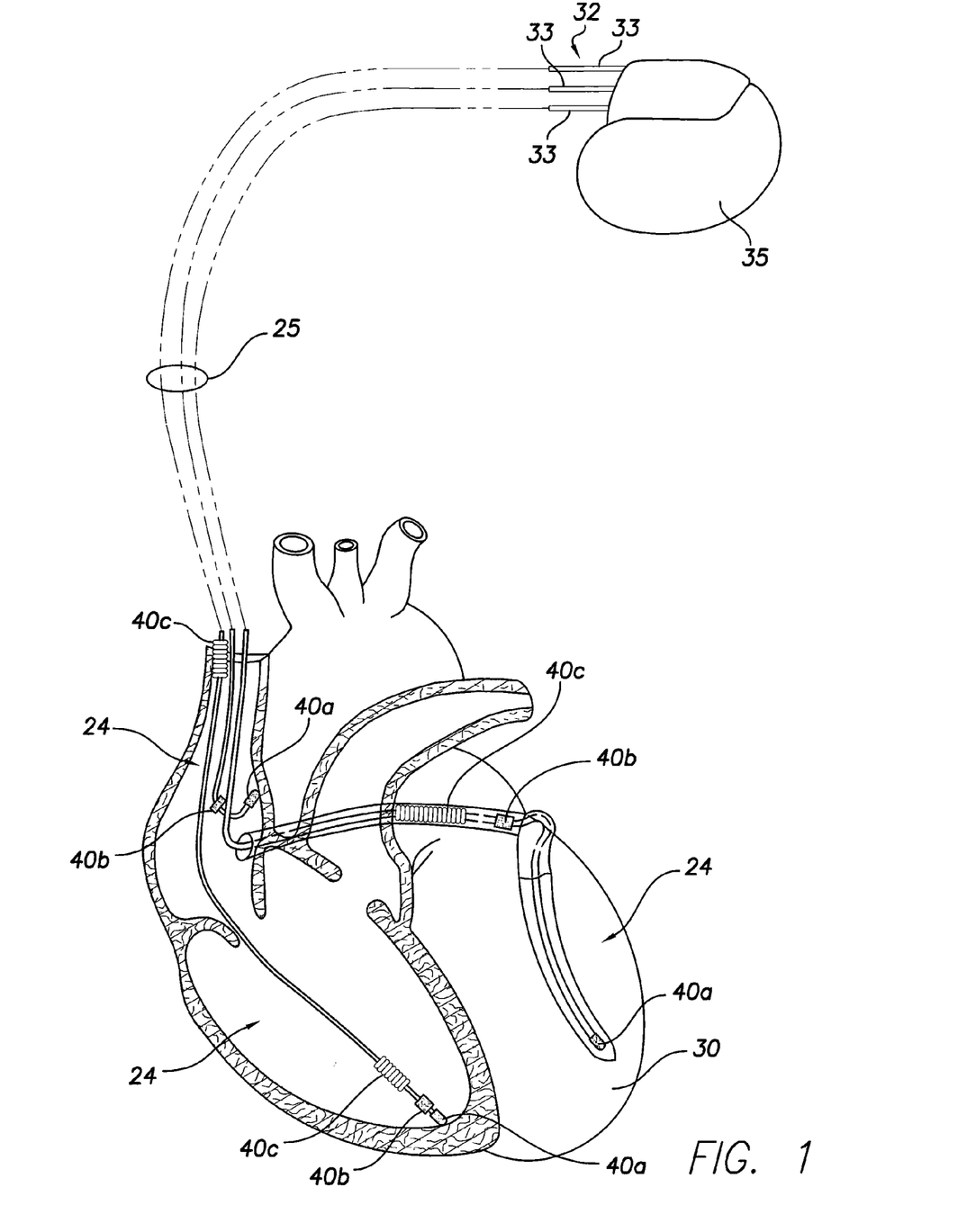
FIG. 1 is a schematic view of a cardiac electrotherapy device according certain embodiments.
Figure 2:
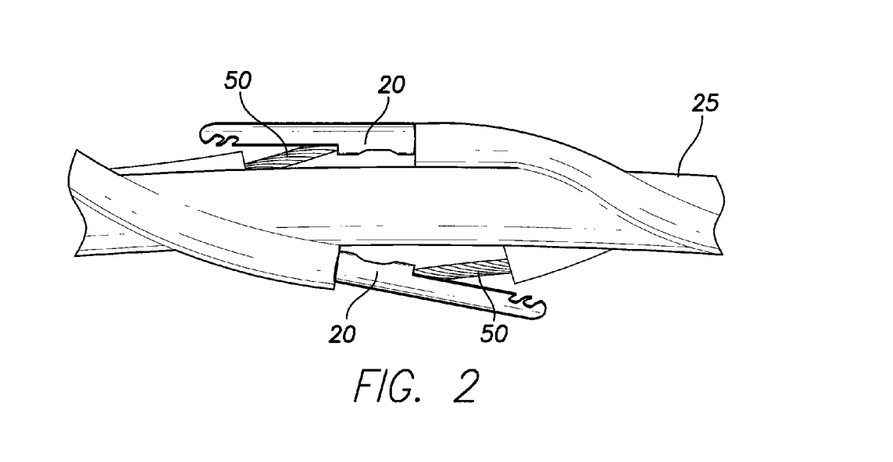
FIG. 2 is an enlarged view of a lead with two crimp connectors in place on opposing conductors, according to certain embodiments.

The following detailed description relates to connectors 20 or terminations used on conductor cables 50 of implantable medical leads 25, such as, for example, cardiac electrotherapy leads (e.g., cardiac resynchronization therapy ("CRT") leads, bradycardia leads, and tachycardia leads) and other types of leads, such as those employed in nerve stimulation for pain management, etc. An implantable medical lead 25 may be used to monitor and stimulate heart function. As shown in FIG. 1, a distal end 24 of a lead 25 may be placed within the heart 30 and a proximal end 32 may be connected to a controller 35 such as a pacemaker, ICD or other type of pulse generator via a lead connector end 33 on the proximal lead end 32. The distal end of the lead 25 may have a series of electrodes 40 including a pacing electrode 40a, a sensing electrode 40b, and a shocking electrode or coil 40c. Each of the electrodes 40 may be connected via a connector 20 to a respective cable conductor 50 or series of cable conductors 50. For example, as shown in FIG. 2, two connectors 20 are shown in position on separate cable conductors 50 and are adapted for connection to a microcoil electrode. The cable conductors 50 may extend the length of the lead 25 to a proximal end 32 of the lead 25 where the cable conductor 50 may be mechanically and electrically coupled to the controller 35.

The cable conductors 50 extending the length of the lead 25 may include a conductive core covered by an insulation layer or layers. As such, the connection between the connector 20 and the cable conductor 50 may require removing or penetrating the insulation to provide a positive electrical connection between the two. The present disclosure is directed at the connectors 20 used to connect cable conductors 50 to shock coils or electrodes 40, other cable conductors 50, and other devices.

In some embodiments, as disclosed below, the connector 20 may be in the form of a crimp connector. The crimp connector allows for the cable conductors 50 to pass into the connector 20 such that the connector 20 may then be squeezed, pressed, or otherwise caused to grasp the cable conductor 50 or conductors 50, restraining them from slipping out of the crimp connector. Moreover, in order to effectively transmit electrical current, the crimp connector may either penetrate the cable conductor insulation or the insulation may be otherwise stripped prior to crimping to create a positive electrical connection. The crimp connector may in turn be welded or otherwise connected to electrodes, shock coils, or other devices, to complete the electrical circuit.

Figure 3:
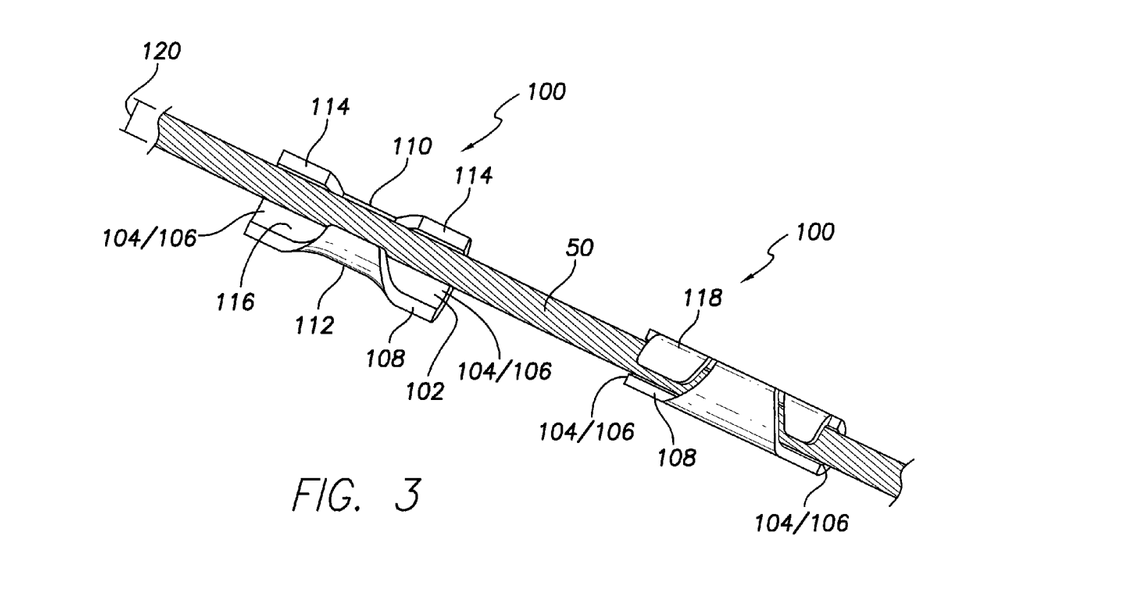
FIGS. 3-7 each show views of parallel connecting crimp connectors in a pre-crimp position and a post-crimp position, according to certain embodiments.

Referring now to FIG. 3, a crimp connector 100, according to certain embodiments is shown. The crimp connector 100 is shown on the left in a pre-crimp position and on the right in a post-crimp position. As shown, the crimp connector 100 includes a body portion 102 with a longitudinal axis, a proximal end 104, 106, a distal end 104, 106, a first lateral edge 108 and a second lateral edge 110. Additionally, first and second edge features 112, 114 are included along respective first and second lateral edges 108, 110.

The body portion 102 of the crimp connector 100 may include a generally rectangular piece of material. The body portion 102 may have a generally uniform thickness and may include a portion of a tube or may be sheet stock material. As such, the body portion 102 may be formed from cutting a tube, stamping sheet stock material, or other fabrication methods known in the art. In one embodiment, the body 102 may be cut, stamped or otherwise formed from a continuous feed of material in the form of tape. In a pre-crimp position, the body 102 may be flat or may have a slightly concave inner surface 116 and a correspondingly convex outer surface 118. In the case of a body 102 formed from a tube, the concave inner surface 116 may reflect the curvature of the inner radius of the tube. In the case of a body 102 formed from a relatively flat plate, the body portion 102 may be rolled, pressed, or otherwise formed to have a concave inner surface 116. Depending on the crimping device used, a concave inner surface 116 and convex outer surface 118 may cause the body 102 to be more readily adapted for the crimping process.

The proximal and distal ends 104, 106 of the connector 100 may be generally squared off ends as would reflect a laser cut, sheared, or punched edge. As such, the proximal and distal ends 104, 106 may take on a generally annular shape in a post-crimp position. A line connecting the center of the proximal annular shape and the center of the distal annular shape may define a post-crimp longitudinal axis. In some embodiments, the proximal end 104, 106 and the distal end 104, 106 are reversible allowing for installation in either orientation. In other embodiments, features may extend from the proximal and/or distal end 104, 106 for attachment to devices. In these embodiments, the orientation may or may not be reversible.

The first and second lateral edges 108, 110 of the connector 100 may be generally parallel to one another and may be generally perpendicular to both the proximal and distal ends 104, 106 so as to form the generally rectangular body portion 102 described. The lateral edges 108, 110 may be generally squared off edges, similar to the proximal and distal ends 104, 106, as would reflect a laser cut, sheared, or punched edge.

As shown, first and second edge features 112, 114 are shown extending from each of the first and second lateral edges 108, 110. The first and second edge features 112, 114 are shown to correspond to one another such that they may interleave with one another when placed in opposing position and advanced toward one another. As shown, the first edge feature 112 includes generally trapezoidal projections in spaced apart relationship creating corresponding trapezoidal void spaces between the projections. Additionally, the second edge feature 114 also includes generally trapezoidal projections in spaced apart relationship creating corresponding trapezoidal void spaces between the projections. The projections and void spaces of the first and second edge features 112, 114 shown have similar spacing but are staggered relative to the opposing edge features 112, 114 along the length of their respective first and second lateral edges 108, 110. This staggered position allows for the projections on the first and second edge feature 112, 114 to coincide with a void space on the respective other edge feature 112, 114. Additionally, the trapezoidal projections taper from relatively wide at the connection to the lateral edge 108, 110 of the body 102 to relatively narrow at the free edge of the projection. As such, the corresponding void spaces taper from relatively narrow at the lateral edge 108, 110 of the body 102 to relatively wide near the free edge of the projections.

Figure 4:
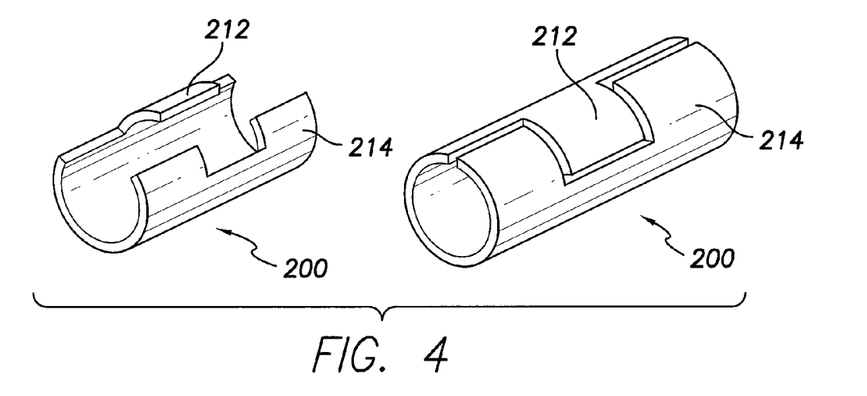
Figure 5:
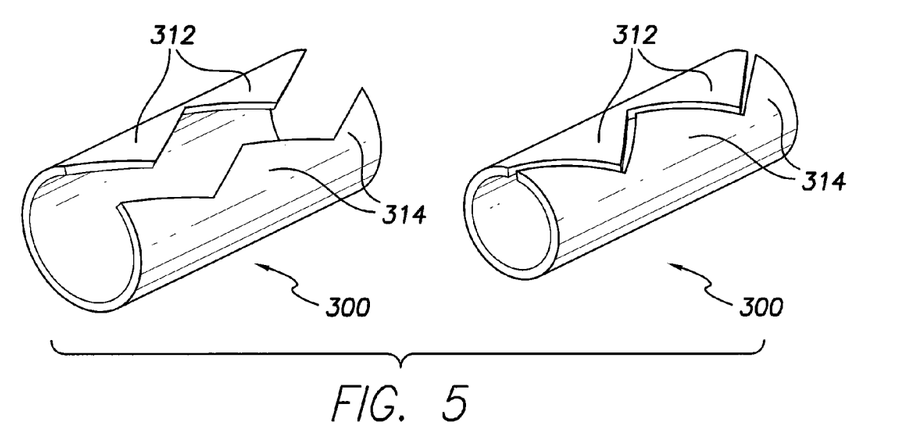
Figure 6:
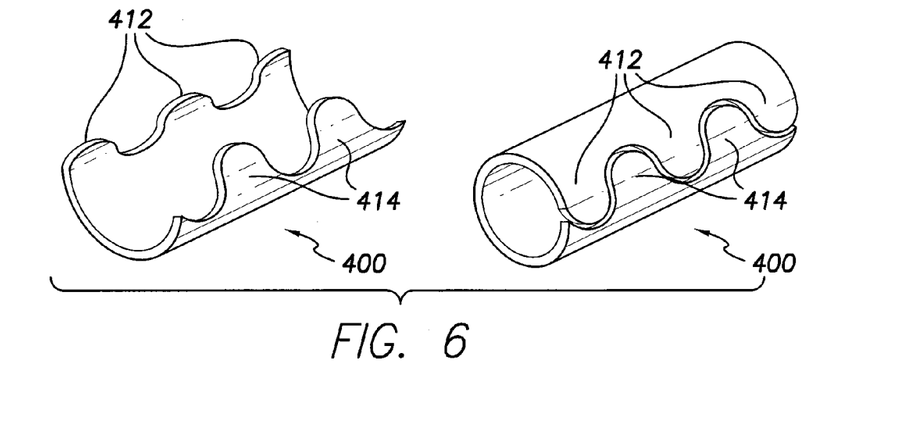
Figure 7:
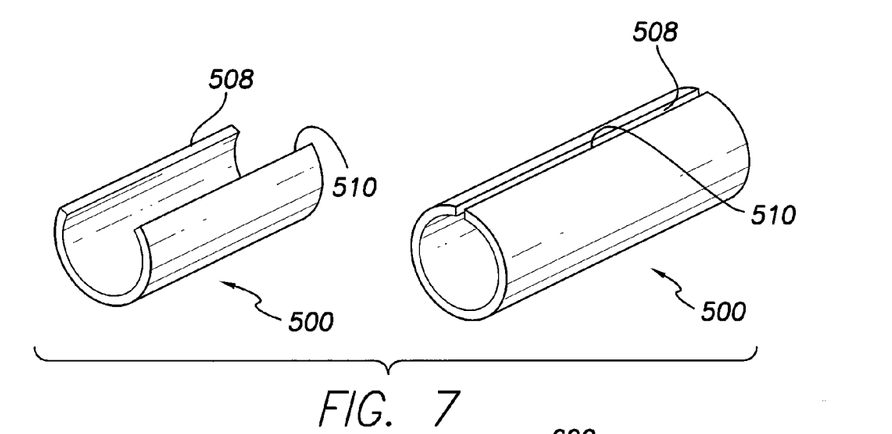

Those of skill in the art will understand and appreciate that several geometries for interleaving edge features are within the scope of the present disclosure. For example, as shown in FIGS. 4-6, staggered rectangular projections are shown for the edge features 212, 214 on crimp connector 200, triangular projections are shown for the edge features 312, 314 on crimp connector 300, and rounded/wave-like projections are shown for the edge features 412, 414 on crimp connector 400. Moreover, the degree of interleaving may be adjusted by increasing or decreasing the length of the projections. Additionally, where the projections are defined by a sloping line such as shown in FIG. 3, 5, or 6, the angle of inclination of the line may be increased or decreased thereby adjusting the projections from long thin projections to short wide projections or any variation in between. Any shape may be used for the projections and asymmetrical shapes and designs may also be used. Where no edge feature is provided, a crimp connector 500 may appear as shown in FIG. 7, where lateral edges 508, 510 have no edge feature.

As will be recognized by comparing the pre-crimp position to the post-crimp position in FIG. 3, or any of FIGS. 3-6, when the crimp connector 100 is crimped and the body 102 is squeezed around a cable conductor 50, the lateral edges 108, 110 of the crimp connector 100 may be brought into opposing position. As such, the projections of the first and second edge features 112, 114 may pass laterally into the void spaces of the opposing edge feature 112, 114 creating the interleaved position of the first and second edge features 112, 114 shown in the post crimp position.

It is noted that the crimp connector 100 shown in FIG. 3 may be assembled with a cable conductor 50 from a parallel position. That is, while a cable conductor 50 may be fed through the crimp connector 100 in the pre-crimp position, the crimp connector 100 may also be assembled by approaching the cable conductor 50 from the side. In this condition, the longitudinal axis of the crimp connector 100 may be positioned parallel to the cable conductor 50 to allow the crimp connector 100 to receive the cable 50 through the space 120 between the edge features 112, 114.

Figure 8:
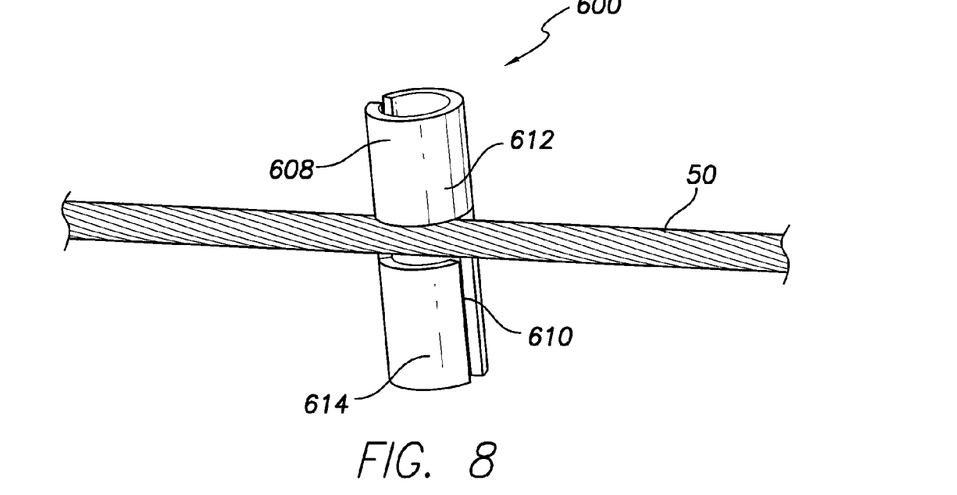
FIGS. 8 and 9 are views of a cross-wise connecting crimp connector shown in an initial pre-crimp stage of assembly and a final pre-crimp stage of assembly, according to certain embodiments.
Figure 9:
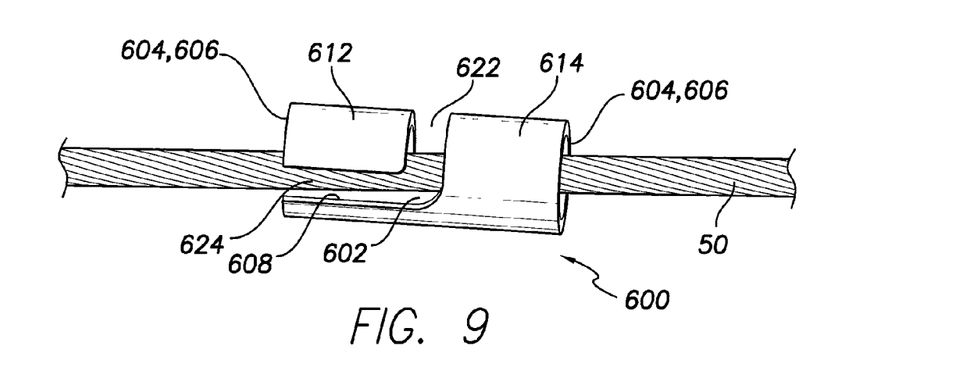

Referring now to FIGS. 8 and 9, a cross-wise crimp connector 600 is shown. In this embodiment, the crimp connector 600 includes a body 602, a proximal end 604, 606, a distal end 604, 606, a first lateral edge 608, and a second lateral edge 610. Additionally, a first and second edge feature 612, 614 is shown in the form of a single projection and a single void space.

In the present embodiment, the body 602 is generally tubular. More particularly, the body 602 reflects approximately one half of a tube with an inner radius. As such, the lateral edges 608, 610 of the body define an included angle 626 of approximately 180 degrees.

First and second edge features 612, 614 are included on the first and second lateral edges 608, 610 of the body 602. The projections of the edge features 612, 614 are generally rectangular with rounded corners and a concave inner surface. The curvature of the concave inner surface, in this embodiment, may be substantially similar to the curvature defined by the inner radius of the tube defining the body 602. In the pre-crimp position, the projections of the first and second edge features 612, 614 extend substantially all the way to the opposing first or second lateral edge 608, 610, such that the free edge of the projection is positioned adjacent to the opposing lateral edge 608, 610, but stops short of contacting the opposing lateral edge 608, 610 a distance approximately equal to the width of a cable conductor 50. Additionally, the projections of the first and second edge features 612, 614 are spaced along the longitudinal length of the body 602 relative to one another to provide for a gap 622 between the opposing projections, the gap 622 being approximately equal to the width of a cable conductor 50. As such, the projections of the first and second edge feature 612, 614 are interleaved similar to those of FIGS. 3-6, but have space between them.

As shown in FIG. 8, the crimp connector 600 of this embodiment may be assembled from a perpendicular position. That is, while a cable conductor 50 may be fed through the crimp connector 600 in a pre-crimp position, the connector 600 may also be assembled by approach the cable conductor 50 from the side. In this condition, the longitudinal axis of the crimp connector 600 may be positioned perpendicular to the cable conductor 50 to allow the gap 622 between the projections of the edge features 612, 614 to receive the cable 50. Once positioned on the cable 50, the crimp connector 600 may be pivoted to bring the longitudinal axis of the connector 600 in approximate alignment with the longitudinal axis of the conductor cable 50. As the connector 600 pivots, the cable conductor 50 may pass through the gaps 624 between the free end of the projections and the opposing lateral edge 608, 610 of the body 602.

Figure 10A:
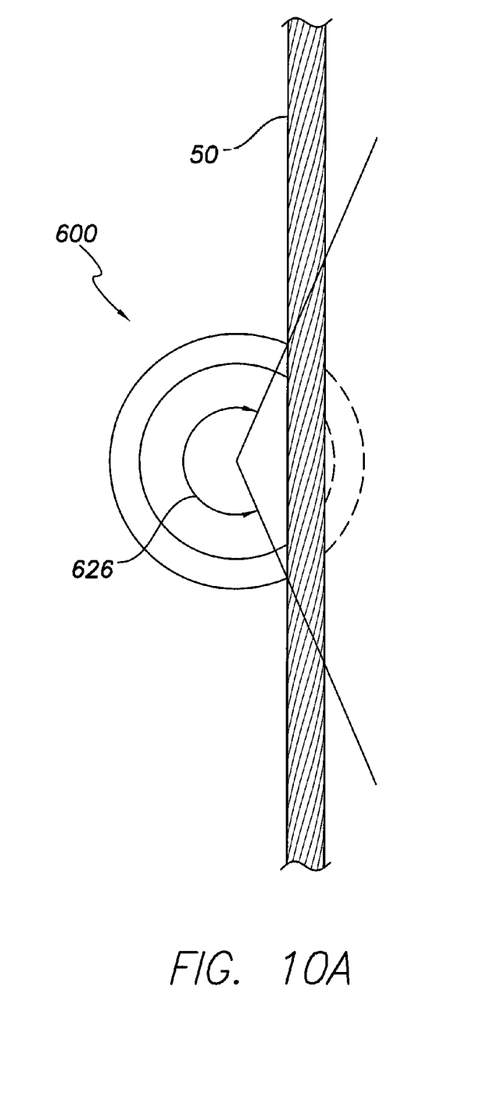
FIGS. 10A and 10B are views of a cross-wise connecting crimp connector showing the included angle, according to certain embodiments.
Figure 10B:
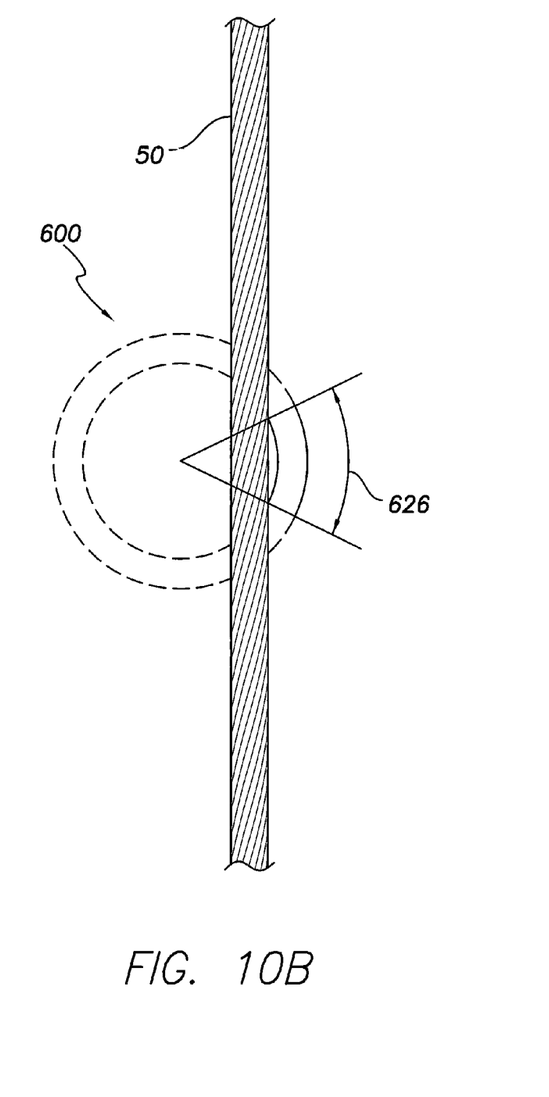

Those of skill in the art will understand and appreciate that the body 602 in this embodiment may vary from defining an included angle 626 of 180 degrees. That is, as shown in FIG. 10, the included angle 626 may be increased or decreased from 180 degrees. In some embodiments, this included angle 626 is limited to avoid interference of the cable conductor 50 with the inside surface of the connector 600 when it is pivoted from its perpendicular to longitudinal position. That is, as shown in FIG. 10A, to the extent that the included angle 626 is increased beyond that shown, the cable conductor 50 may begin to interfere with the inner surface of the connector 600 near the free ends of the projections. In FIG. 10B, to the extent that the included angle 626 is decreased beyond that shown, the cable conductor 50 may begin to interfere with the inner surface of the connector 600 near the lateral edges 608, 610 of the body 602 where they oppose the free ends of the projections. It is also noted, however, that the cable conductor 50 may be flexed from the straight position shown in FIGS. 10A and 10B, to accommodate greater or lesser included angles 626 of the body 602.

It is also noted that the relatively rectangular edge features 612, 614 of the present embodiment, may deviate to more trapezoidal shaped edge features 612, 614 by modifying the edge of the projections which are positioned adjacent to one another. That is, rather than the gap 622 between the two projections being oriented substantially perpendicular (e.g. 90 degrees) to the longitudinal axis of the connector 600, the gap 622 may be oriented somewhere between 0 and 90 degrees.

The tube internal diameter and slot widths may be varied as necessary to accommodate conductor configurations of a variety of conductor sizes or diameters and of a range of number of conductors.

While not shown, the body portion of any of the described embodiments may also include splice openings similar to those described in U.S. patent application Ser. No. 12/363,445, filed Jan. 30, 2009, titled "Crimp-Through Crimp Connector for Connecting a Conductor Cable and an Electrode of an Implantable Cardiac Electrotherapy Lead", the contents of which are hereby incorporated by reference herein.

Figure 11:
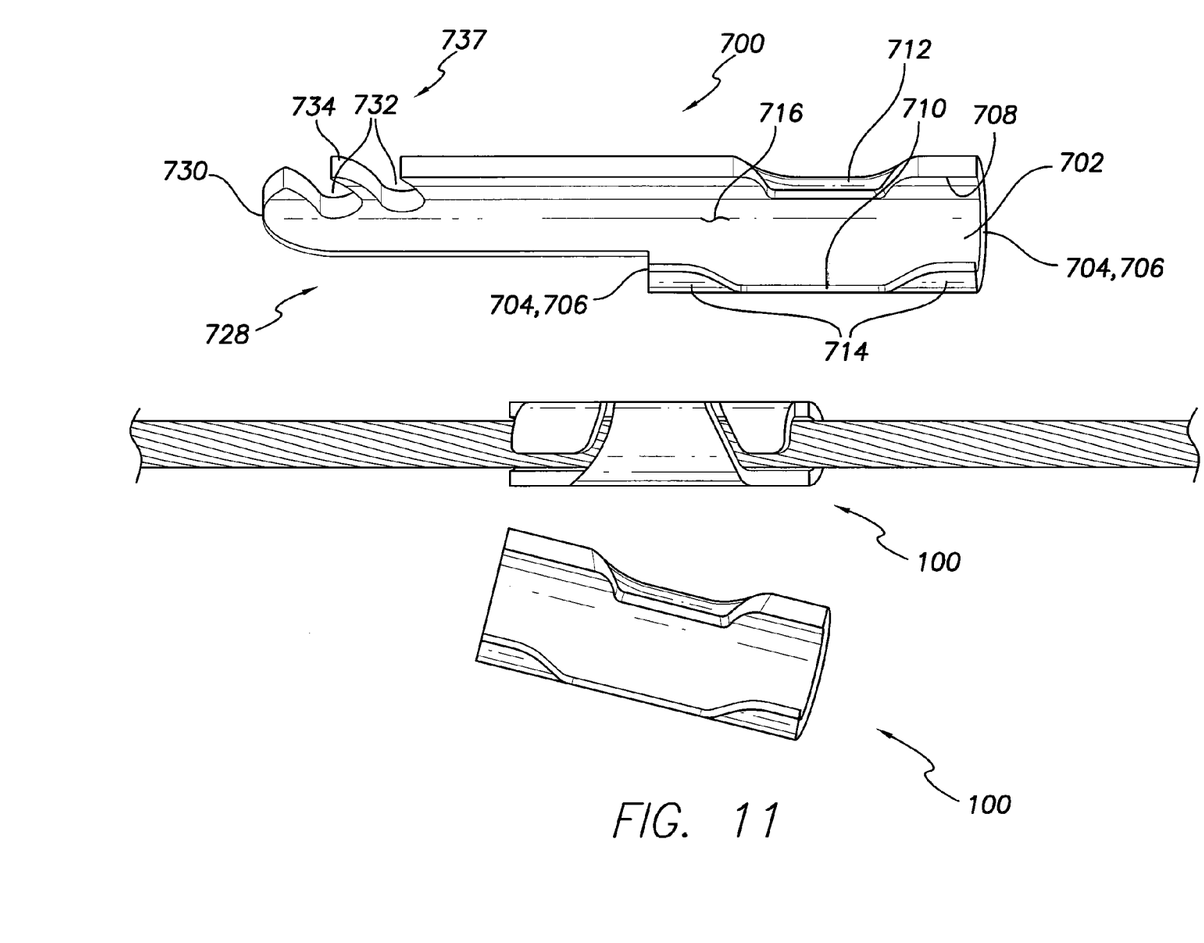
FIG. 11 shows a basic crimp connector in a pre-crimp position and a post-crimp position as well as a crimp connector with a termination feature, according to certain embodiments.
Figure 12A:
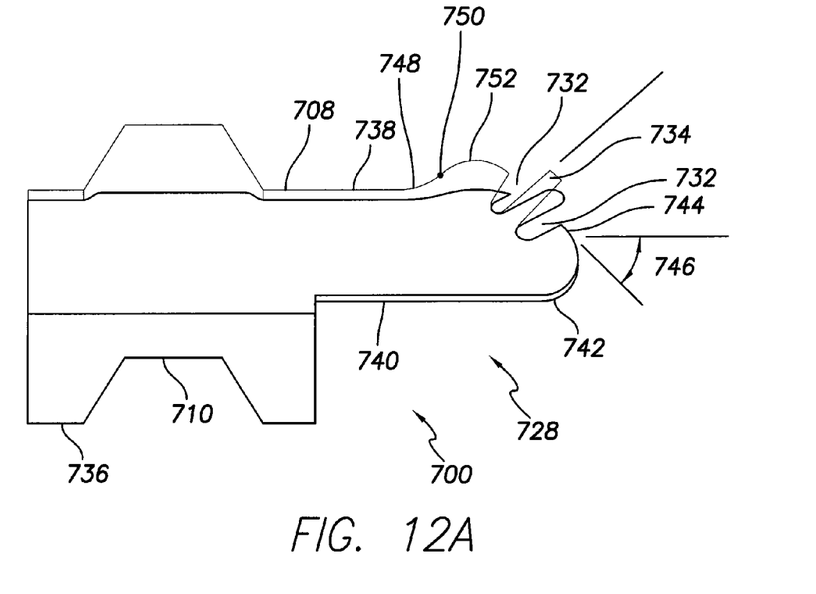
FIGS. 12A-12D show several views of a crimp connector with a termination feature, according to certain embodiments.
Figure 12B:
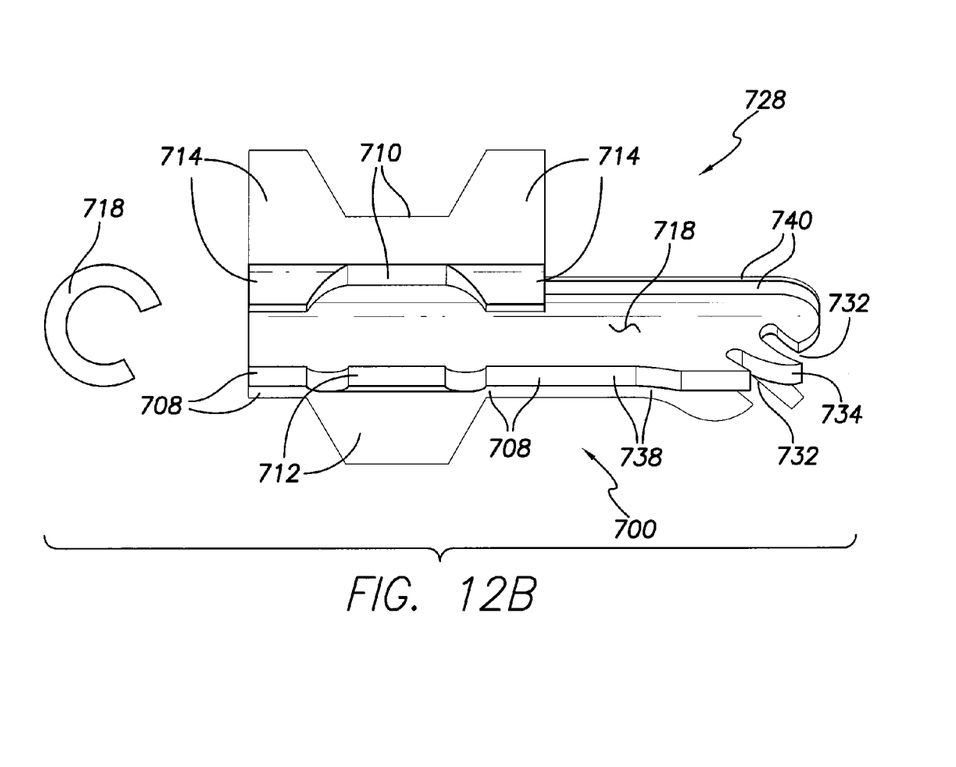
Figure 12C:
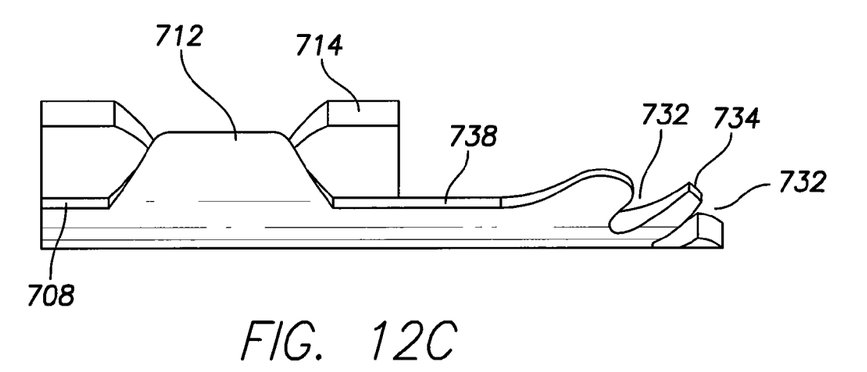
Figure 12D:
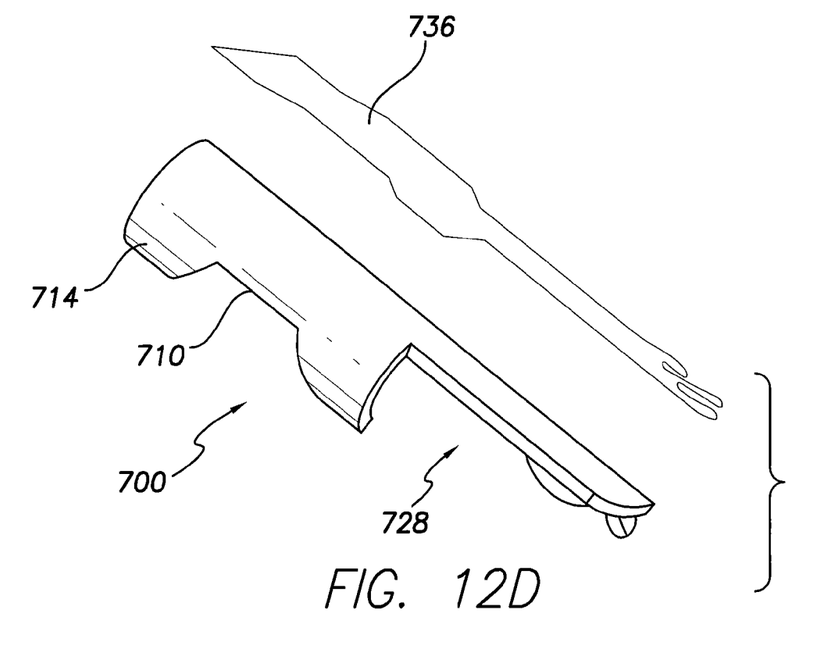

Referring now to FIGS. 11-12D, yet another embodiment of a crimp connector is shown. FIG. 11 shows a crimp connector 700 in comparison to the crimp connector 100 previously described. The crimp connector 700, includes an extension 728 integral with the body 702 of the connector and extending from a proximal or distal end 704, 706 of the body 702. The extension 728, in this embodiment, extends as a segment of the body 702 and maintains the inner and outer surface contours associated with the body 702. That is, where the inner surface 716 of the body 702 is concave, the extending inner surface of the extension 728 is also concave. The extension 728 extends in a longitudinal direction and has a smaller width than that of the body 702, the width of the extension 728 and the body 702 being measured perpendicular to the lateral edges 708, 710 of the body 702. The extension may be of any shape or form, including an external electrode surface.

The free end 730 of the extension 728 has a generally rounded edge with two notches 732 in the lateral edge of the extension 728. The two notches 732 form a peninsula-like feature 734 there between. The two notches 732 and the peninsula-like feature 734 create a termination feature 737 in the form of a microcoil attachment feature.

FIGS. 12A-12D show several views of the crimp connector 700 and include diagrams of how to form the connector 700 from a flat piece of material 736. As best shown in FIGS. 12A and 12B, the extension 728 of the connector 700 in a flat pre-formed condition includes two relatively straight parallel sides 738, 740, the first side 738 extending from and parallel to the first lateral edge 708 of the body 702 and the second side 740 extending from a point between the lateral edges 708, 710 of the body 702. The second side 740 extends toward the free end of the extension 728 and terminates in a radiused curve 742 wrapping around the end of the extension 728 until it aligns with a skewed face 744 defined by an angle 746. The first side extends 738 toward the free end of the extension 728 and terminates in a first radiused 748 curve diverging from the centerline of the extension. The first radiused curve 748 then terminates at an inflection point 750 where a second radiused curve 752 then wraps around the end of the extension 728 until it aligns with the skewed face 744 defined by the angle 746. The skewed face 744 includes two U-shaped notches 732 separated by a trapezoidal shaped peninsula 734, which extends beyond the limit of the skewed face 744. As shown in FIGS. 12A-12D, the crimp connector may be formed to create a concave inner surface 718 and thus create a pre-crimp position for the connector 700.

As can be understood from FIG. 12D, the crimp connector 700 may be formed from a flat piece of material 736 and then curved to have curved inner and outer surfaces. In other embodiments, the crimp connector 700 may be cut from a tubular body, such that the crimp connector may have curved inner and outer surfaces without further modification.

Figure 13:
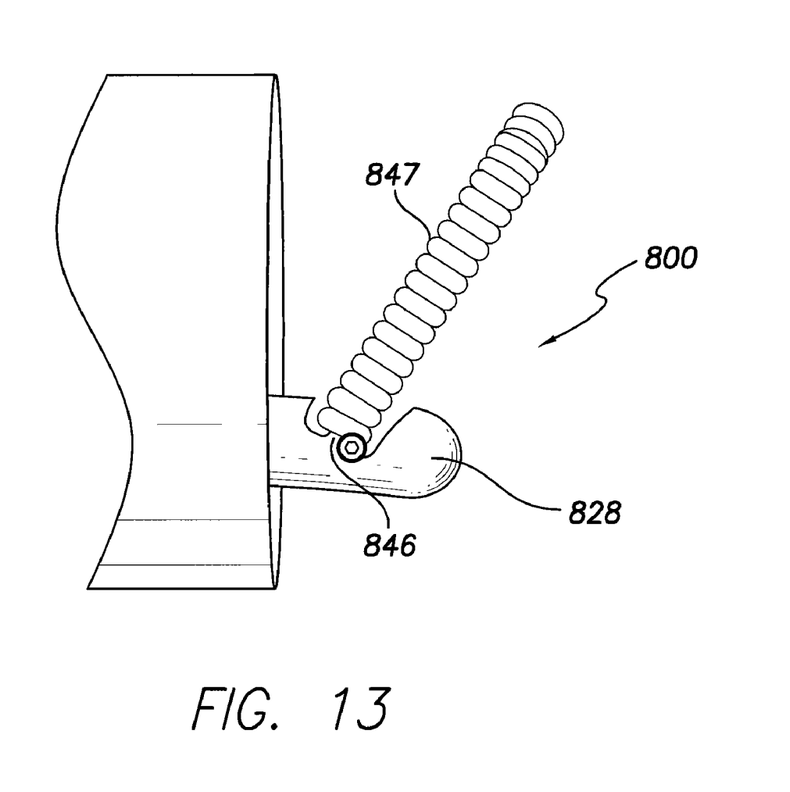
FIG. 13 shows a view of a crimp connector with a spike feature or secondary attachment point, according to certain embodiments configured for micro-coil attachment.

FIG. 13 shows yet another embodiment of a crimp connector 800. In this embodiment, the crimp connector 800 includes a microcoil attachment spike 846 on the outer surface of the crimp extension 828. The secondary attachment point 846, which may be in the form of a spike or other feature, may be used for the attachment of a micro-coil 847 to the crimp connector 800.

Figure 14:
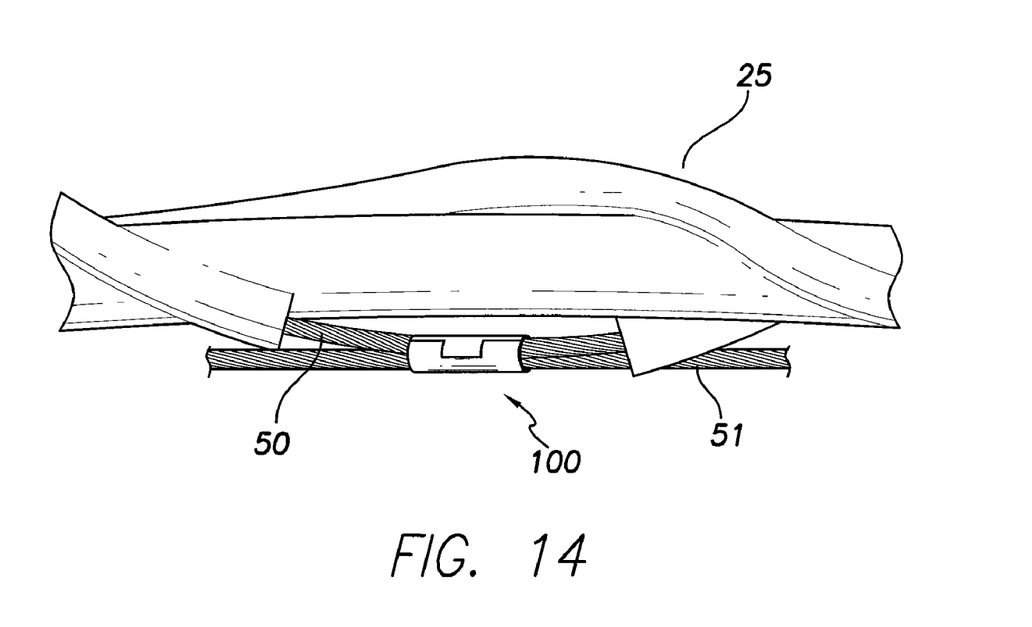
FIG. 14 shows a crimp connector on a lead crimping a primary conductor to a secondary conductor.

FIG. 14 shows a crimp connector 100 in position on a medical lead 25. In this embodiment, the crimp connector 100 is shown securing a primary cable conductor 50 to a secondary cable conductor 51. Such a crimp connector 100 may be employed for a connection to a wire, pin or tab in a similar fashion.

Figure 15:
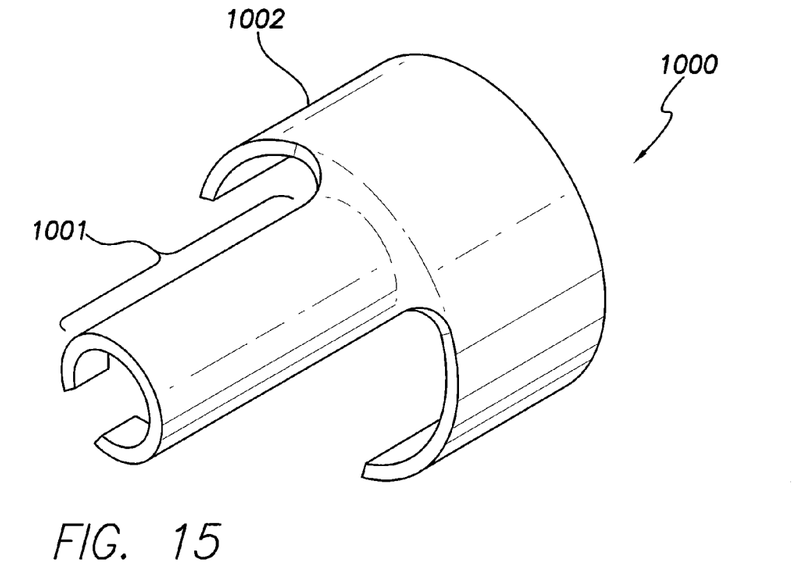
FIG. 15 is an isometric view of such an integral, single-piece or unitary body crimp connector equipped electrode.
Figure 16:
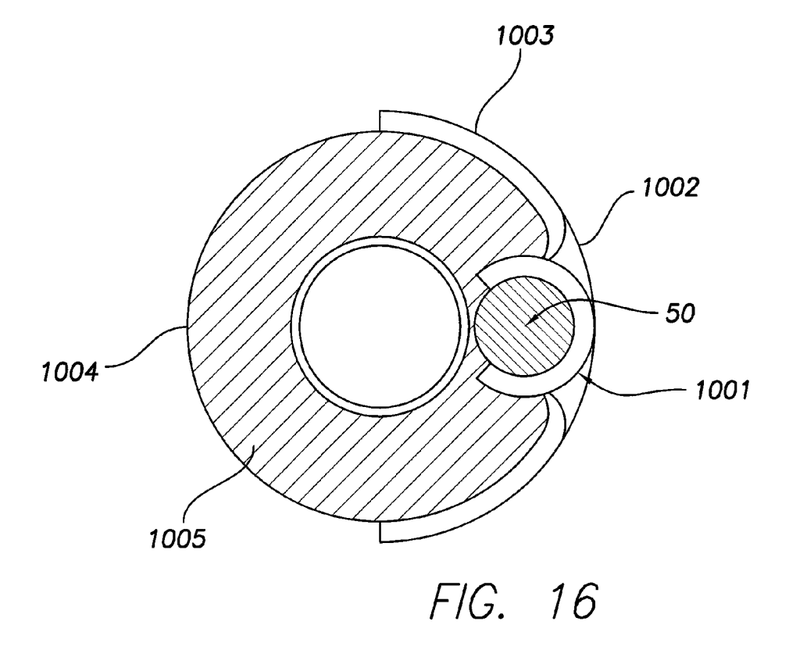
FIG. 16 is a cross section of a lead employing the integral, single-piece or unitary body crimp connector equipped electrode of FIG. 15.

In one embodiment, any one or more of the above-described crimp connector configurations may be an extension of an electrode such that the electrode and crimp connector form an integral, single-piece or unitary body. For example, as can be understood from FIG. 15, which is an isometric view of such an integral, single-piece or unitary body crimp connector equipped electrode 1000, the electrode 1000 includes a crimp portion 1001 and an electrode portion 1002. The electrode portion 1002 may be in the form of a ring electrode, partial ring electrode or other configuration. The crimp portion 1001 may be configured the same as the crimp connectors 100 discussed above with respect to FIGS. 4, 5 and 6 or any of the other crimp connectors 100 described above. The crimp portion 1001 may extend proximally from a proximal edge of the electrode portion 1002. As can be understood from FIG. 15 and as more particularly shown in FIG. 16, which is a cross section of a lead 25, the crimp portion 1001 may be positioned radially inward relative to the outer circumferential surface 1003 of the electrode portion 1002 and the outer circumferential surface 1004 of the lead body insulation 1005. Such a configuration of the crimp portion 1001 relative to the electrode portion 1002 allows the crimp portion 1001, and the cable conductor 50 received in the crimp portion 1001, to be recessed within the lead body insulation 1005 as the crimp portion 1001 and cable connector 50 extend proximally towards the lead connector end from the electrode portion 1002.

Those of skill in the art will understand and appreciate the advantages associated with a side loading crimp connector. In the case of multiple conductors, for example, the more conductors involved, the more difficult it may become to thread them through a crimp connector. This may be due to insufficient space within the crimp connector combined with a tendency for the cable conductors to catch on one another as they are threaded through. This may make longitudinal positioning of the cable conductors difficult and may also lead to abrading neighboring conductors in locations along their length where it is desired to have full insulation protection.

Additionally, the interleaving edge features disclosed above may provide for a tight-fitting, smooth-wrapping band about the conductor. In the post-crimped position, the gaps or spaces between the edge features may be closed to a point that the crimp connector reflects a smooth cylinder with little to no evidence of seams.

Other advantageous situations may include medical leads having space constraints due to electronics being included within electrode bands. Additionally, some lead bodies do not lend themselves to threading of conductors through crimp connectors. For example, U.S. patent application Ser. No. 12/400,564, filed Mar. 9, 2009, titled "Implantable Medical Lead Having a Body with Helical Cable Conductor Construction and Method of Making Same", the contents of which are hereby incorporated by reference herein, describes a helical lead with multiple point terminations of conductors and a multi-band lead configuration, which both make it difficult to string conductors through connectors.

Although the present invention has been described with reference to preferred embodiments, persons skilled in the art will recognize that changes may be made in form and detail without departing from the spirit and scope of the invention.

What is claimed is:

1. An implantable medical lead comprising:
a cable conductor extending along the lead; and
a cross-wise crimp connector secured to the cable conductor, the crimp connector comprising:
a body with an outer surface, an inner surface, proximal and distal ends, and first and second lateral edges, the lateral edges having edge features extending there from, the edge features adapted to opposingly interleave with one another, the body defining a longitudinal axis;
a first gap between the interleaved projections, the gap extending substantially perpendicular to the longitudinal axis of the body; and
a second gap between the free end of the projections and the opposing lateral edge of the body;
wherein the first and second gaps have a width substantially equal to the width of the cable conductor;
wherein the crimp connector is adapted for cross-wise assembly with the cable conductor;
wherein the longitudinal axis of the body is positioned perpendicular to a longitudinal axis of the cable conductor to allow the first gap to receive the cable conductor; and
wherein the body is subsequently pivoted to allow the second gap to receive the cable conductor and to bring the longitudinal axis of the body in alignment with the longitudinal axis of the cable conductor.

2. The lead of claim 1, wherein the edge features comprise staggered complimentary projections.

3. The lead of claim 2, wherein the crimp connector has a pre-crimp position with a concave inner surface and the edge features extending from the first and second lateral edges are positioned with a space between their respective free edges.

4. The lead of claim 3, wherein the projections are generally rectangular.

5. The lead of claim 3, wherein the projections are generally trapezoidal.

6. The lead of claim 1, wherein the body is a portion of a tube with a length and an included angle, the tube defining the longitudinal axis of the body.

7. The lead of claim 6, wherein the included angle is approximately 180 degrees.

8. The lead of claim 7, wherein the projections are generally rectangular in shape.

9. The lead of claim 8, wherein the crimp connector has two projections.

10. The lead of claim 7, wherein the projections are generally trapezoidal in shape.

11. The lead of claim 2, further comprising an extension attached to and extending from the distal or proximal end of the body.

12. The lead of claim 11, wherein the extension includes a free end opposite the attachment to the body, the extension further comprising a termination feature on the free end.

13. The lead of claim 12, wherein the termination feature is a microcoil attachment feature.

14. The lead of claim 1, wherein crimp conductor further comprises an electrode portion, the crimp conductor and electrode portion forming a single-piece unitary body.

* * * * *